United States Patent
Min et al.

(10) Patent No.: US 7,976,504 B1
(45) Date of Patent: Jul. 12, 2011

(54) NEEDLE CATHETER WITH AXIALLY ELONGATING AND CONTRACTING NEEDLE

(75) Inventors: Sung-Woo Min, Fremont, CA (US); William Jason Fox, San Carlos, CA (US); Jesus Magana, Redwood City, CA (US)

(73) Assignee: Abbott Cardiovascular Systems Inc., Santa Clara, CA (US)

( * ) Notice: Subject to any disclaimer, the term of this patent is extended or adjusted under 35 U.S.C. 154(b) by 0 days.

(21) Appl. No.: 12/112,992

(22) Filed: Apr. 30, 2008

(51) Int. Cl.
*A61M 5/00* (2006.01)

(52) U.S. Cl. ......... 604/171; 604/172; 604/272; 604/273

(58) Field of Classification Search ................. 604/171, 604/172, 164.01, 164.12, 164.04, 164.07, 604/272, 273, 198
See application file for complete search history.

(56) References Cited

U.S. PATENT DOCUMENTS

| | | | |
|---|---|---|---|
| 3,890,977 A * | 6/1975 | Wilson .................. | 604/531 |
| 4,465,072 A | 8/1984 | Taheri | |
| 5,324,273 A | 6/1994 | Discko, Jr. | |
| 5,353,800 A | 10/1994 | Pohndorf et al. | |
| 5,531,713 A | 7/1996 | Mastronardi et al. | |
| 5,665,072 A * | 9/1997 | Yoon .................. | 604/164.12 |
| 5,762,632 A * | 6/1998 | Whisson .............. | 604/171 |
| 6,540,724 B1 | 4/2003 | Harris | |
| 6,592,552 B1 * | 7/2003 | Schmidt .............. | 604/164.01 |
| 6,595,958 B1 * | 7/2003 | Mickley .............. | 604/164.01 |
| 6,855,124 B1 * | 2/2005 | Gonzalez et al. ...... | 604/96.01 |
| 7,112,208 B2 | 9/2006 | Morris et al. | |
| 2007/0167665 A1 | 7/2007 | Hermann et al. | |

OTHER PUBLICATIONS

Oesterle et al., "Percutaneous in Situ Coronary Venous Arterialization, Report of the First Human Catheter-Based Coronary Artery Bypass", Circulation 103, pp. 2539-2543 (2001).
U.S. Appl. No. 12/022,047, filed Jan. 29, 2008, Chan et al.

* cited by examiner

*Primary Examiner* — Kevin C Sirmons
*Assistant Examiner* — Larry R Wilson
(74) *Attorney, Agent, or Firm* — Squire, Sanders & Dempsey (US) LLP

(57) ABSTRACT

A needle catheter with an axially elongating and contracting needle and methods of using for delivering therapeutic materials to the heart are disclosed.

20 Claims, 2 Drawing Sheets

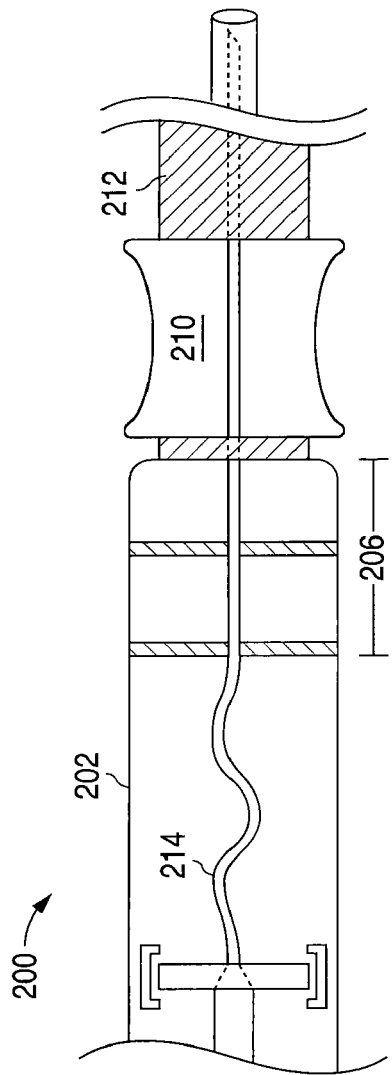
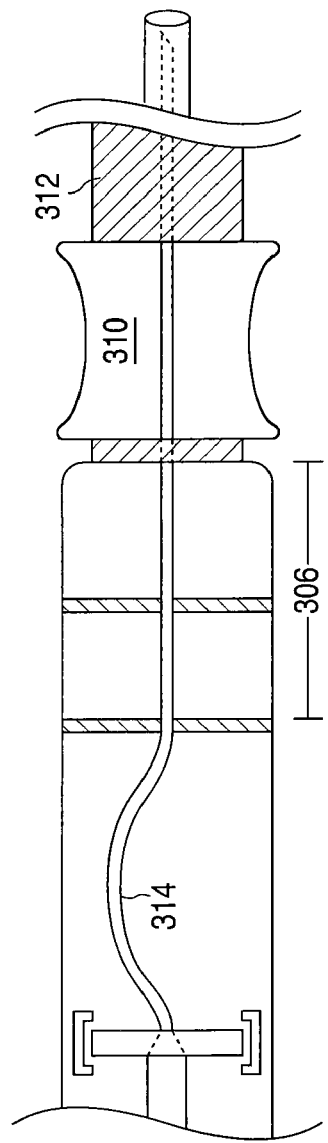
FIG. 2
FIG. 3

NEEDLE CATHETER WITH AXIALLY ELONGATING AND CONTRACTING NEEDLE

FIELD OF THE INVENTION

The present invention is directed to a needle catheter with an axially elongating and contracting needle.

BACKGROUND OF THE INVENTION

Needle injection catheters are used for the delivery of cells or other biologic or therapeutic materials into various internal organs including the heart. The needle component spans the length of the catheter and functions as a fluid transport lumen to transport an injectable material from the proximal end of the catheter to the distal end of the catheter where the needle tip acts to inject the material into the target tissue. In order to puncture the tissue, the needle must be extended from the catheter. It must be retracted and sheathed, however, in order to effectively deliver the end of the catheter to the target area. Thus, the use of needle catheters require that the ends of the fluid transport lumen, that is the needle tip and the injection luer fitting at the proximal end of the catheter, must be moved relative to each other.

In commonly used needle catheters, a handle shell surrounds a needle, a manifold, a septum and a fluid lumen. The fluid lumen interacts with a luer fitting at the proximal end of the handle where it is can be attached to a syringe containing cells or other biologic or therapeutic materials. The fluid lumen also interacts with the manifold and septum in the middle region of the handle at which point it is coupled to the needle. Once the distal end of a catheter is positioned at a target tissue, the needle is extended by moving the needle relative to the manifold and fluid lumen while a fluid tight seal is maintained by the septum. The needle is retracted by reversing the process. These systems, however, are costly, difficulty to manufacture and prone to leakage.

There is a need in the art, therefore, for novel needle catheter assemblies that are easy to manufacture and less prone to leakage.

SUMMARY OF THE INVENTION

The present invention relates to a needle catheter that includes a hollow handle comprising a proximal end, a distal end and a lumen extending from the proximal end to the distal end, a movable knob disposed on a rod that is attached to the distal end of the handle and a needle comprising a reversibly deformable material positioned within the handle, wherein the proximal end of the needle is operatively coupled to a proximal hub that is positioned in the proximal end of the handle and a medial part of the needle runs centrally through the rod and movable knob such that when the knob is moved the needle moves with it.

In various aspects, the reversibly deformable material can be nitinol, stainless steel, cobalt chromium, nylon, urethane, polyurethane, polyvinylchloride or polyester.

In various aspects, a fluid lumen is operatively coupled to the proximal end of the needle at the proximal hub which is positioned at the proximal end of the handle.

In various aspects, the proximal end of the needle is coupled to the proximal hub by adhesive bonding, thermal welding or press fitting.

In various aspects, when the movable knob is positioned adjacent to the distal end of the handle the needle is substantially coiled, bowed or wave-shaped. In various aspects, the shape of the needle is formed by heat treatment.

Another aspect of the present invention relates to a method for delivering therapeutic materials into heart tissue that involves providing a needle catheter according to the invention, providing a therapeutic material and administering the therapeutic material into the heart tissue.

BRIEF DESCRIPTION OF THE DRAWINGS

FIG. 1A shows the knob in a position adjacent to the distal end of the handle wherein the needle is substantially coiled. FIG. 1B shows the knob positioned away from the distal end of the handle wherein the needle is extended.

FIG. 2 depicts the handle section of a needle catheter showing the knob in a position adjacent to the distal end of the handle wherein the needle is substantially wave-shaped.

FIG. 3 depicts the handle section of a needle catheter showing the knob in a position adjacent with to the distal end of the handle wherein the needle is substantially bowed.

DETAILED DESCRIPTION

As used herein, the use of the singular includes the plural and visa versa unless expressly stated otherwise. That is, "a" and "the" are to be construed as referring to one or more of whatever the word modifies.

As used herein, "catheter" refers to a tube that can be inserted into a body cavity, duct or vessel allowing for the injection of fluids, access to internal organs by surgical instruments, e.g., a needle, or the placement of implantable medical devices, e.g., a stent. A catheter can be a thin, flexible tube, i.e., a soft catheter, or a larger solid tube, i.e., a hard catheter.

As used herein, "needle" refers to a hollow tube with a sharp distal end used to inject substances into a tissue.

As used herein, "needle catheter" refers to a catheter in which a needle is disposed such that the needle can be delivered to a site within the body in order to inject a therapeutic material into a target tissue.

As used herein, "tissue" generally refers to any group of cells that in the aggregate perform the same function and specifically refers to tissues that receive blood through a dedicated arterial system, such tissues including the lungs (pulmonary artery), liver (hepatic artery), kidneys (renal artery) and heart (coronary artery).

As used herein, "lumen" refers to a cavity of a tubular structure including an organ such as a blood vessel or a device such as a catheter or catheter handle.

Figure 1A:
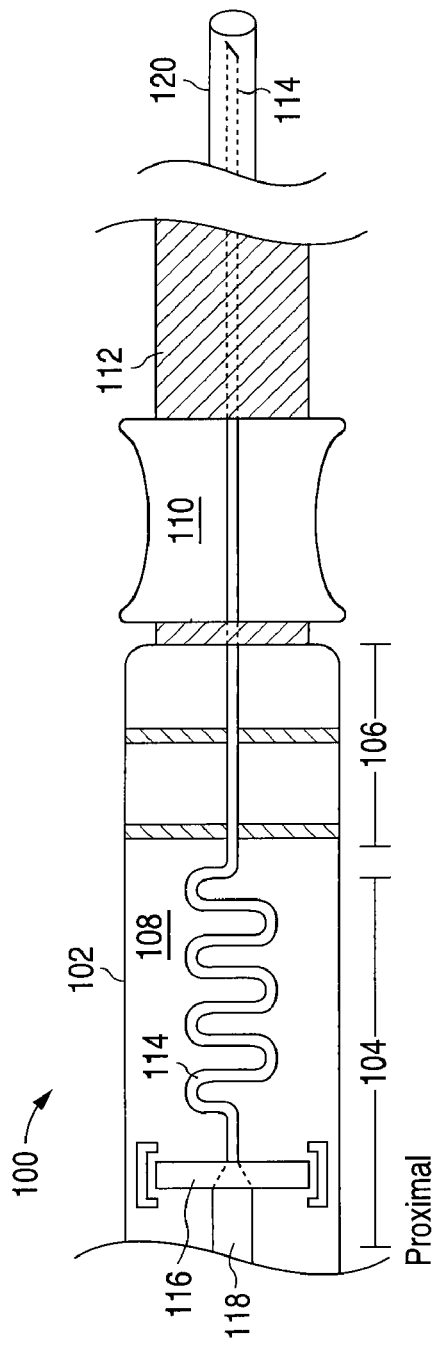
FIGS. 1A-B depict the handle section of a needle catheter of the invention.
Figure 1B:
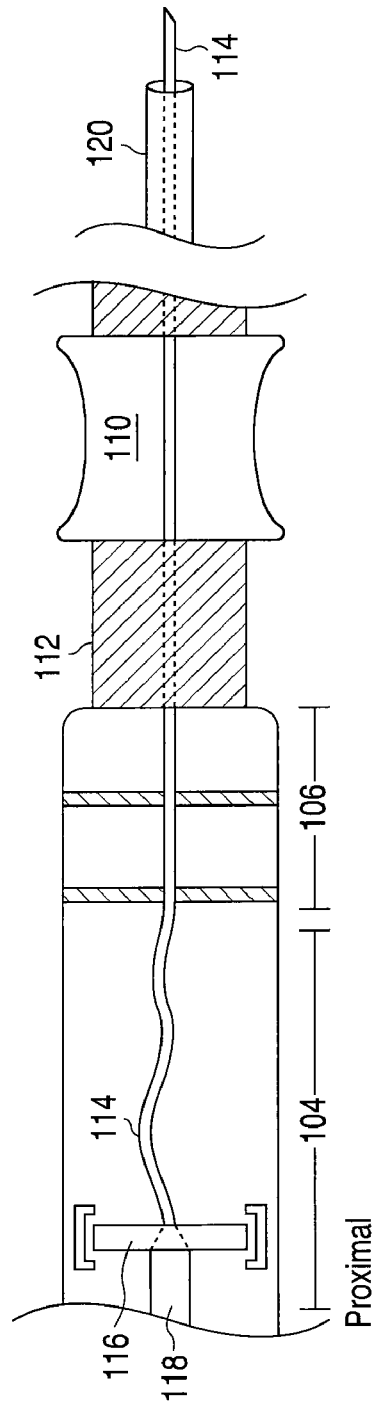

As used herein, "reversibly deformable material" refers to any material that can be repeatedly induced to change shape upon the application of a specific stimulus to the material, e.g., pressure or heat, yet upon removal of the stimulus will return to its original shape. It is to be understood that a stimulus appropriate for the present invention includes sliding the knob over the rod, as depicted in FIGS. 1A and 1B. Examples of reversibly deformable materials suitable for the present invention include, without limitation, nitinol, stainless steel, cobalt chromium, nylon, urethane, polyurethane, polyvinylchloride and polyester.

As used herein, "operatively coupled" refers to the attachment of a needle of the invention to either the proximal hub or the fluid lumen of the needle catheter through direct or indirect means, respectively. For example, it is possible for the needle to be coupled to the proximal hub directly, e.g., through adhesive bonding, thermal welding or press fitting. Alternatively, it is possible for the needle to be coupled to the fluid lumen indirectly such that the needle would attach to an intermediate component, e.g., the proximal hub, which in turn would be coupled to the fluid lumen, as depicted in the figures herein.

As used herein, "adhesive bonding" refers to a method where two materials, e.g., metals, plastics or composites, are joined using an adhesive, e.g., glue or epoxy.

As used herein, "thermal welding" refers to a method where two materials, e.g., metals, plastics or composites, are joined by heating one or both of the materials and fusing the materials together so that upon cooling, the materials are effectively bonded together.

As used herein, "press fitting" refers to the attachment of two components by friction. For example, the proximal end of a needle can be compressed so that it fits into a slightly larger component orifice, e.g., a proximal hub, at which point the proximal end of the needle is allowed to return to its normal size, thereby being held tight by the orifice.

As used herein, "substantial" or "substantially" refers to a characteristic of the object of the adverb by which it is understood that the object is not a perfect example as such would be immediately envisaged by the reader. Rather, when modified by the word "substantially," the object of the modifier would be considered close enough to those of ordinary skill in the art to warrant the object designation.

As used herein, "substantially coiled" refers to the shape of a needle that resembles a spiral or corkscrew shape.

As used herein, "substantially bowed" refers to the shape of a needle that resembles a bow or curved shape.

As used herein, "substantially wave-shaped" refers to the shape of a needle that resembles a sinusoidal curve.

The present invention relates to a needle catheter that includes a needle made of a reversibly deformable material. The needle is positioned within the catheter such that it can be delivered to a site within a body in a retracted position but upon being positioned at the target tissue is able to be extended to inject cells or any biologic or therapeutic substance into the tissue.

FIGS. 1A-B show a first aspect of the invention. FIG. 1A shows a knob and handle section of needle catheter 100 of the invention. Hollow handle 102 includes proximal end 104, distal end 106 and lumen 108 extending from proximal end 104 to distal end 106. Movable knob 110 is disposed on rod 112 which is positioned adjacent to distal end 106 of handle 102 such that knob 110 can slide back and forth along rod 112. Needle 114 is positioned inside of handle 102 and the proximal end of needle 114 is operatively coupled to proximal hub 116 which is positioned in proximal end 104 of handle 102. At proximal hub 116, needle 114 is operatively coupled to fluid lumen 118.

When knob 110 is positioned on rod 112 adjacent to distal end 106, needle 114 will be in a substantially coiled shape, as shown in FIG. 1A. It is in this position that distal end 120 of catheter 100 can be moved through the vasculature to a target tissue since needle 114 will be in a retracted position. When knob 110 is moved along rod 112 to become positioned away from distal end 106, needle 114 will straighten, to some extent as depicted in FIG. 1B, so that the sharp distal end of needle 114 can penetrate a tissue once the catheter is in position. It is to be understood that both before and after knob 110 is moved, fluid, e.g., a therapeutic substance, can flow from fluid lumen 118 through proximal hub 116 and into needle 114. It has been determined that the coil of the needle does not significantly change the fluid dynamics within the needle.

Because needle 114 is made of a reversibly deformable material, when knob 110 is moved back into a position adjacent to distal end 106, i.e., the position depicted in FIG. 1A, needle 114 will reform into a substantially coiled shape. It is to be understood that needle 114 can be used any number of times for the delivery of fluids and that after the needle is extended it will return to is original shape.

FIG. 2 and FIG. 3 show alternative embodiments of the invention. FIG. 2 depicts knob 210 and handle section 202 of needle catheter 200 of the invention in which needle 214 is present in a substantially waved formation. FIG. 3 depicts another embodiment of the invention in which needle 314 is substantially bowed. It is to be understood, however, that when knob 210 or 310 is moved along rod 212 or 312 away from distal end 206 or 306 needle 214 and 314 will straighten, to some extent as depicted in FIG. 1B, so that the sharp distal end of the needle can penetrate a tissue once the catheter is in position. When knob 210 and 310 are moved back into a position adjacent to distal end 206 or 306 of the handle, needle 214 and 314 will reform into either a substantially waved or a substantially bowed shape, respectively. It is to be understood that the needle catheter components depicted in FIGS. 1, 2 and 3 are the same, e.g., knob 110 is the same as knob 210 and 310. Needles 114, 214 and 314, however, are different as depicted in FIGS. 1A, 2 and 3.

Another aspect of the present invention relates to a method for delivering therapeutic materials into heart tissue that involves providing a needle catheter according to the invention, providing a therapeutic material and administering the therapeutic material into the heart tissue.

The therapeutic material, also referred to herein as a drug or biologic material, can include cells as well as an antiproliferative agent, an anti-inflammatory agent, an antineoplastic, an antimitotic, an antiplatelet, an anticoagulant, an antifibrin, an antithrombin, a cytostatic agent, an antibiotic, an anti-allergic agent, an anti-enzymatic agent, an angiogenic agent, a cyto-protective agent, a cardioprotective agent, a proliferative agent, an ABC A1 agonist, an antioxidant or any combination thereof.

It is to be understood that methods of using a needle catheter according to the invention for the administration of therapeutic materials to heart tissue will be easily ascertainable to those skilled in the art from the disclosures herein.

While particular embodiments of the present invention have been shown and described, it will be obvious to those skilled in the art that changes and modifications can be made without departing from this invention in its broader aspects. Therefore, the appended claims are to encompass within their scope all such changes and modifications as fall within the true spirit and scope of this invention.

What is claimed is:

1. A needle catheter comprising:
   a hollow handle comprising a proximal end, a distal end and a lumen extending from the proximal end to the distal end;
   a movable knob disposed on a rod, the rod attached to the distal end of the handle;
   a needle comprising a reversibly deformable material positioned within the handle, wherein the proximal end of the needle is operatively coupled to a proximal hub that is positioned in the proximal end of the handle and a medial part of the needle runs centrally through the rod and the movable knob such that when the knob is moved the needle moves with it.

2. The needle catheter according to claim 1, wherein the reversibly deformable material comprises nitinol, stainless steel, cobalt chromium, nylon, urethane, polyurethane, polyvinylchloride or polyester.

3. The needle catheter according to claim 1, wherein a fluid lumen is operatively coupled to the proximal end of the needle at the proximal hub positioned at the proximal end of the handle.

4. The needle catheter according to claim 1, wherein the proximal end of the needle is coupled to the proximal hub by adhesive bonding, thermal welding or press fitting.

5. The needle catheter according to claim 1, wherein when the movable knob is positioned adjacent to the distal end of the handle, and the needle is substantially coiled, bowed or wave-shaped.

6. The needle according to claim 1, wherein the reversibly deformable material is formed by heat treatment.

7. A method for delivering therapeutic materials into heart tissue comprising:
   providing a needle catheter according to claim 1;
   providing a therapeutic material; and
   administering the therapeutic material into heart tissue using the needle catheter.

8. The needle catheter according to claim 1, wherein the knob is adapted to slide backward and forward along the rod.

9. The needle catheter according to claim 8, further comprising a tube surrounding the needle, the needle adapted to move in the tube when the knob is slid backward and adapted to move out of the tube when the knob is slid forward.

10. The needle catheter according to claim 1, further comprising a catheter portion adapted for insertion into an anatomical body part, wherein the needle is at least partially disposed inside the catheter portion.

11. The needle catheter according to claim 10, wherein the needle is movable from a retracted position to an extended position such that a tip of the needle is disposed inside the catheter portion when the needle is in the retracted position and the tip of the needle is disposed outside the catheter portion when the needle is in the extended position.

12. A needle catheter comprising:
   a handle;
   a tube adapted for insertion into an anatomical body part;
   a knob movable relative to the handle, the knob disposed between the handle and the tube; and
   a needle comprising a reversibly deformable rear segment at least partially disposed inside the handle and a forward segment at least partially disposed inside the tube, the needle connected to the knob in such a way that when the knob is moved away from the handle a tip of the forward segment moves from a retracted position within the tube to an extended position outside the tube.

13. The needle catheter of claim 12, further comprising a rod disposed between the handle and the tube, the knob adapted to slide back and forth along the rod.

14. The needle catheter of claim 12, further comprising a proximal hub at a proximal end of the handle, wherein a proximal end of the needle is coupled to a proximal hub by adhesive bonding, thermal welding or press fitting.

15. The needle catheter of claim 12, wherein when the tip moves from the retracted position to the extended position outside the tube, the rear segment of the needle straightens to some extent from a curved shape.

16. The needle catheter of claim 12, wherein the needle includes a proximal end and the reversibly deformable rear segment of the needle is disposed between the proximal end and the knob.

17. The needle catheter according to claim 1, wherein the reversibly deformable material is disposed between the movable knob and the proximal hub.

18. The needle catheter of claim 1, wherein the rod extends out from an outer surface of the handle.

19. The needle catheter of claim 12, wherein the knob is movable between a distal end of the handle and the tube.

20. The needle catheter of claim 13, wherein the rod extends out from an external surface of the handle.

* * * * *